United States Patent
Tahara et al.

(10) Patent No.: US 6,482,405 B1
(45) Date of Patent: Nov. 19, 2002

(54) IN SITU INJECTION OF ANTIGEN-PRESENTING CELLS WITH GENETICALLY ENHANCED CYTOKINE EXPRESSION

(75) Inventors: Hideaki Tahara, Tokyo (JP); Michael T. Lotze, Pittsburgh, PA (US); Yasuhiko Nishioka, Tokushima (JP)

(73) Assignee: University of Pittsburgh of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 09/395,836

(22) Filed: Sep. 14, 1999

Related U.S. Application Data (60) Provisional application No. 60/100,048, filed on Sep. 15, 1998.

(51) Int. Cl.[7] .............. A61K 48/00; A61K 31/00; C12N 15/74; C12N 5/02; C12N 5/00
(52) U.S. Cl. ........... 424/93.21; 424/93.2; 435/320.1; 435/325; 435/360; 435/372; 435/383; 435/384; 435/385; 514/44
(58) Field of Search ............... 435/320.1, 325, 435/360, 372, 383, 384, 385; 514/44; 424/93.2, 93.21

(56) References Cited

U.S. PATENT DOCUMENTS

| | | | |
|---|---|---|---|
| 5,674,486 A | 10/1997 | Sobol et al. | 424/93 |
| 5,681,562 A | 10/1997 | Sobol et al. | 424/93.21 |
| 5,962,318 A | * 10/1999 | Rooney et al. | 435/325 |
| 5,962,320 A | 10/1999 | Robinson | 435/366 |

FOREIGN PATENT DOCUMENTS

| WO | WO 99/30734 | 6/1999 |
|---|---|---|

OTHER PUBLICATIONS

Lotze et al, The Cancer Journal of Scientific American, 3: S109–114, 1997.*
Gura, T. Science. 278: 1041–1042, Nov. 1997.*
Verma et al. Nature. 389: 239–242, Sep. 1997.*
Nishioka et al. Cancer Research. 59: 4035–4041, Aug. 1999.*
Ram et al. Nature Medicine, 3(12): 1354–1361, Dec. 1997.*
Yasutomi et. al., A Vaccine–Elicited, Single Viral Epitipe–Specific Cytotoxic T Lymphocyte Response Does Not Protect against Intravenous, Cell–Free Simian Immunodeficiency Virus Challenge, 1995, Journal of Virology, 2279–2284.*
Ross et. al., Gene Therapy in the United States: A five–year status report, 1996, Human Gene Therarpy,7: 1781–1790.*
Haung et. al., Role of Bone Marrow–Derived Cells in Presenting MHC Class1–Restricted Tumor Antigens, 1994, Science, vol. 264: 961–965.*
Fuchs et al., B Cells Turn Off Virgin But Not Memory T Cells, 1992, Sciencemvol. 258: 1156–1159.*

Gilbert et. al., Tolerogenicity of Resting and Activated B Cells, 1994, J. Exp. Med. vol. 179: 249–258.*
Vieweg et. al., Considerations for the use of Cytokine–Secreting Tumor Cell Preparations for Cancer Treatment, 1995, Clinical Science Review 13(2): 193–201.*
Orkin et. al., Report and Recommendations of the Panel to Assess the NIH Investment in Research on Gene Therapy, 1995.*
Ahuja et al., "Human Dendritic Cell (DC)–Based Anti–Infective Therapy: Engineering DCs to Secrete Functional IFN–γ and IL—12[1]", The Journal of Immunology, vol. 161, No. 2, pp. 868–876, Jul. 15, 1998.
Arthur et al., "A Comparison of Gene Transfer Methods in Human Dendritic Cells", Cancer Gene Therapy, vol. 4, No. 1, pp. 17–25, 1997.
Tüting et al., "Autologous Human Monocyte–Derived Dendritic Cells Genetically Modified to Express Melanoma Antigens Elicit Primary Cytotoxic T Cell Responses In Vitro: Enhancement by Cotransfection of Genes Encoding the Th1–Biasing Cytokines IL–12 and IFN–α[1]", The Journal of Immunology, vol. 160, No. 3, Feb. 1, 1998.
Zitvogel et al., Adjuvants (Gene Therapy), "IL–12 Engineered Dendritic Cells Serve as Effective Vaccine Adjuvants In Vitro and In Vivo", Gene Therapy Weekly, pN/A, Dec. 11, 1995.
Ahuja et al., "Dentritic Cell (DC)–Based Anti–Infective Strategies: DCs Engineered to Secrete IL–12 Are a Potent Vaccine in a Murine Model of an Intracellular Infection", Journal of Immunology, Oct. 1, 1999, vol. 163, No. 7, pp. 3890–3897.
Bramson et al., "Direct Intratumoral Injection of an Adenovirus Expressing Interleukin–12 Induces Regression and Long–Lasting Immunity that is Associate with Highly Localized Expression of Interleukin–12", Human Gene Therapy, Oct. 20, 1996, vol. 7, pp. 1995–2002.
Melero et al., "Intratumoral Injection of Bone–Marrow Derived Dendritic Cells Engineered to Produce Interleukin–12 Induces Complete Regression of Established Murine Transplantable Colon Adenocarcinomas", Gene Therapy, Oct. 10, 1999, vol. 6, No. 10, pp. 1779–1784.

(List continued on next page.)

Primary Examiner—A. M. S. Beckerleg
(74) Attorney, Agent, or Firm—Testa, Hurwitz & Thibeault, LLP (57) ABSTRACT

The use of professional antigen presenting cells genetically modified to enhance expression of an immunostimulatory cytokine is disclosed for the treatment of individuals having tumors or infections. The genetically modified professional antigen presenting cells are injected directly at or near the site of the tumor or infection. Preferred professional antigen presenting cells include dendritic cells, and preferred immunostimulatory cytokines include interleukins such as IL-12.

10 Claims, 7 Drawing Sheets

OTHER PUBLICATIONS

Nishioka et al., "Induction of Systemic and Therapeutic Antitumor Immunity Using Intratumoral Injection of Dendritic Cells Genetically Modified to Express Interleukin 12", Cancer Research, Aug. 15, 1999, vol. 59, No. 16, pp. 4035–4041.

Strokus et al., "Genetically–modified dendritic cells serve as effective adjuvants in promoting antitumor immunity in vitro and in vivo" FASEB Journal, 1996, vol. 10, No. 6, pp. A1443, abstract.

Tahara et al., "Fibroblasts Genetically Engineered to Secrete Interleukin 12 Can Suppress Tumor Growth and Induce Antitumor Immunity to a Murine Melanoma in Vivo", Cancer Research, vol. 54, Jan. 1, 1994, pp. 182–189.

Arai et al: Complete Nucleotide Sequence of the Chromosomal Gene for Human IL–4 and Its Expression, The Journal of Immunology, vol. 142, Jan. 1, 1989; 274–282.

Banchereau et al: Dendritic Cells and the Control of Immunity, Nature vol. 392: Mar. 19, 1998; 245–252.

Cantrell et al: Cloning, Sequence, and Expression of a Human Granulocyte/Macrophage Colony–Stimulating Factor, Proc. Natl. Acad. Sci, USA, vol. 82, Sep. 1985; 6250–6254.

Caux et al: CD34 Hematopoietic Progenitors from Human Cord Blood differentiate Along Two Independent Dendritic Cell Pathways in Response to GM–CFS + TNFα, J. Exp. Med., vol. 184, Aug. 1996; 695–706.

Chambers et al: Long Term Expression of IL–4 In Vivo Using Retroviral–Mediated Gene Transfer, the Journal of Immunology, vol. 149, Nov. 1, 1992; 2899–2905.

Fiers et al: Gene Cloning and Structure–Function Relationship of Cytokines Such as TNF and Interleukins, Immunology Letters, 16, 1987; 219–226.

Gren et al: Novel Human Leukocyte Interferon Subtype and Structural Comparison of Alpha Interferon Genes, Journal of Interferon Research 4, 1984; 609–617.

Henderson et al: Human Dendritic Cells Genetically Engineered to Express High Levels of the Human Epithelial Tumor Antigen Mucin (MUC–1), Cancer Research 56, Aug, 15, 1996: 3763–3770.

Hirano et al: Complementary DNA For a Novel Human Interleukin (BSF–2) That Induces B Lymphocytes to Produce Immunoglobulin, Nature vol. 324: Nov. 6, 1996; 73–76.

Korn et al: Cloning of Genomic DNA for Tumor Necrosis Factor and Efficient Expression in CHO Cells, Lymphokine Research, vol. 7, No. 4, 1988; 349–358.

Lotze: Dendritic Cells as Therapeutic Reagents for the Treatment of Patients With Cancer, Annals of Surgery, vol. 226, No. 1, Jul. 1997; 1–5.

Lotze et al: Cytokine Gene Therapy of Cancer Using Interleukin–12: Murine and Clinical Trials, Annals New York Academy of Sciences; Oct. 1996; 440–454.

Lotze et al: Dendritic Cell Based Therapy of Cancer, Dendritic Cells in Fundamental and Clinical Immunology, 1997; 551–569.

Lotze et al: The Role of Interleukin–2, Interleukin–12, and Dendritic Cells in Cancer Therapy, The Cancer Journal from Scientific American, vol. 3, Supplement 1, 1997; S109–S114.

Mayordomo et al: Bone Marrow–Derived Dendritic Cells Serve as Potent Adjuvants for Peptide–Based Antitumor Vaccines; Stem Cells 1997; 94–103.

Nabel et al: Immunotherapy of Malignancy by In Vivo Gene Transfer into Tumors, Human Gene Therapy 3(1992); 399–410.

Pennica et al: Human Tumour Necrosis Factor: Precursor Structure, Expression and Homology to Lymphotoxin, Nature vol. 312: Dec. 27, 1984; 724–729.

Reeves et al: Retroviral Transduction of Human Dendritic Cells with a Tumor–associated Antigen Gene, Cancer Research 56, Dec. 15, 1996; 5672–5677.

Richards et al: Adenovirus Vectors for Cytokine Gene Expression; Jul. 1995; 282–293.

Romani et al: Proliferating Dendritic Cell Progenitors in Human Blood, J. Exp. Med., vol. 180, Jul. 1994; 83–93.

Specht et al: Dendritic Cells Retrovirally Transduced with a Model Antigen Gene Are Therapeutically Effective Against Established Pulmonary Metastases, The Journal of Experimental Medicine, vol. 186, No. 8, Oct. 20, 1997; 1213–1221.

Tahara et al: Antitumor effects in patients with melanoma, head, neck, and breast cancer in phase I/II clinical trial of interleukin–12 (IL–12) gene therapy, Pro. Am. Soci of Clin. Oncol, vol. 16 439(a) May, 1997.

Tahara et al: Effective eradication of established murine tumors with IL–12 gene therapy using a polycistronic retroviral vector, J. Immunol., 154(12), Jun. 15, 1995; 6466–74.

Tüting et al: Development of Dendritic Cell–Based Genetic Vaccines for Cancer, Dendritic Cells in Fundamental and Clinical Immunology, 1997; 511–518.

Tüting et al: Gene–Based Strategies for the Immunotherapy of Cancer, Journal of Molecular Medicine, 1997; 75:478–491.

Weissmann et al: Primary and Tertiary Structure of Nucleic Acids and Cancer Research—Structure and Expression of Human α–Interferon Genes, Japan Scientific Societies Press, Tokyo, 1982; 1–22.

Wolf et al: Cloning of cDNA for Natural Killer Cell Stimulatory Factor, a Heterodimeric Cytokine With Multiple Biologic Effects on T and Natural Killer Cells, The Journal of Immunology, vol. 146, May 1, 1991; 3074–3081.

Yang et al: Immunotherapeutic Potential of Tumor Antigen–Pulsed and Unpulsed Dendritic Cells Generated from Murine Bone Marrow, Cellular Immunology 179, 1997; 84–95.

Yasukawa et al: Structure and Expression of Human B Cell Stimulatory Factor–2 (BSF–2/IL–6) Gene, The EMBO Journal, vol. 6, No. 10, 1987; 2939–2945.

Zitvogel et al: Cancer immumotherapy of established tumors with IL–12. Effective delivery by genetically engineered fibroblasts, J Immunol., 155(3), Aug. 1, 1995; 1393–403.

Zitvogel et al: IL–12–Engineered Dendritic Cells Serve as Effective Tumor Vaccine Adjuvants in Vivo, Annals New York Academy of Sciences, Oct. 1996; 284–293.

* cited by examiner

Days after tumor inoculation

IN SITU INJECTION OF ANTIGEN-PRESENTING CELLS WITH GENETICALLY ENHANCED CYTOKINE EXPRESSION

RELATED APPLICATIONS

This application claims the benefit of U.S. Provisional Application No. 60/100,048, filed Sep. 15, 1998, now abandoned.

GOVERNMENT RIGHTS IN THE INVENTION

This work was supported in part by Grant Number POI CA59371 from the National Cancer Institute of the National Institutes of Health. The government has certain rights in the invention.

FIELD OF THE INVENTION

The present invention is directed to the field of immunology. In particular, the present invention is directed to the use of genetically-modified professional antigen-presenting cells to combat infections or tumors.

BACKGROUND OF THE INVENTION

Critical analysis of early events in the cellular immune response to tumor and viral antigen have identified dendritic cells as the major antigen-presenting cells (APCs) eliciting an effective T cell response (Steinman (1991), Annu. Rev. Immunol. 9:271–296; Macatonia et al. (1989), J. Exp. Med. 169:1255–1264). Dendritic cells (DCs), appropriately activated, take up soluble antigen and apoptotic bodies, migrate to the paracortical T cell-rich areas of lymph nodes, and initiate a series of interactions leading to the selection of antigen-specific T cells, and to the release of the DC cytokines, interferon-α (IFN-α) and interleukin-12 (IL-12).

It has previously been demonstrated that administration of DCs pulsed with synthetic tumor-associated peptides serve as effective therapeutic antitumor vaccines, inducing an effective antitumor immune response in vitro and following adoptive transfer in mice (Mayordomo et al. (1995), Nature Med. 1:1297–1302; Zitvogel et al. (1996), J. Exp. Med. 183:87–97; Porgador and Gilboa (1995), J. Exp. Med. 182:255–260; Porgador et al. (1996), J. Immunol. 156:2918–2926). However, T cell-defined epitopes have been identified only for a limited number of human tumor types. Several approaches to overcome this problem including pulsing DCs with acid-eluted bulk tumor peptides Zitvogel et al. (1996), tumor extracts and RNA (Flamand et al. (1994), Eur. J. Immunol. 24:605–610; Ashley et al. (1997), J. Exp. Med. 186:1177–1182; Boczkowski et al. (1996), J. Exp. Med. 184:465–472) or fusion of tumor with DC (Gong et al. (1997) Nature Med. 3:558–561) have been employed for DC-based vaccination strategies against tumors. Even though these approaches will allow treatment of tumors for which tumor associated antigen is not well characterized, there are still significant problems, particularly in the preparation of clinical samples from human solid cancers.

IL-12 is a heterodimeric cytokine produced by DCs, macrophages, polymorphonuclear leukocytes and keratinocytes (Lamont and Adorini (1996), Immnunol. Today 17:214–217). IL-12 enhances natural killer (NK) cell and cytotoxic T lymphocyte (CTL) activities, plays a key role in the induction of Th1 immune responses including IFN-γ production, and has IFN-γ/interferon-inducible protein 10 (IP-10)-dependent antiangiogenic effects (Lamont and Adorini (1996), supra; Voest et al. (1995), J. Natl. Cancer Inst. 87:581–586; Sgadari et al. (1996), Blood 87:3877–3882). DCs are capable of producing IL-12 after ligation of CD40 and class II molecules, presumably only following interaction with T cells, and IL-12 delivery in conjunction with DCs enhances CTL response in vitro (Heufler et al. (1996), Eur. J. Immunol. 26:659–668; Koch et al. (1996), J. Exp. Med. 184:741–746; Bhardwaj et al. (1996), J. Clin. Invest. 98:715–722).

There have been reports of potent antitumor effects of IL-12 in a vaccination model with IL-12 gene-modified tumor cells, as well as with systemic administration of IL-12 protein (Brunda et al. (1993), J. Exp. Med. 178:1223–1230; Nastala et al. (1994), J. Immunol. 153:1697–1706; Tahara et al. (1995), J. Immunol. 154:6466–6474; Martinotti et al. (1995), Eur. J. Immunol. 25:137–146). Direct injection of IL-12-transduced fibroblasts also effectively eliminated established tumors with concomitant induction of effective systemic immunity (Zitvogel et al. (1995), J. Immunol. 155:1393–1403). Based on these results, an initial clinical trial of IL-12 gene therapy has been completed using autologous fibroblasts in the context of a phase I study (Tahara et al. (1997), Proc. Am. Soc. Clin. Oncol. 16:439a). Partial responses were observed in patients with melanoma, breast cancer, and head and neck tumors persisting for up to two years.

SUMMARY OF THE INVENTION

The present invention depends, in part, upon the discovery that professional antigen-presenting cells (APCs) which have been genetically modified to enhance expression of an immunostimulatory cytokine, may be directly injected into or near the site of an infection or tumor to induce a specific immunological response against antigens associated with the infection or tumor without pre-loading or pulsing the APCs with the antigens. In particular, it has been found that dendritic cells (DCs), and preferably bone marrow-derived dendritic cells (BM-DCs) or CD34+-derived dendritic cells (CD34+-DCs), which have been genetically modified to enhance expression an immunostimulatory cytokine, preferably interleukin-12 (IL-12), may be injected into or near the site of an infection or tumor to induce a specific immune response against antigens associated with the site of injection.

Therefore, in one aspect, the present invention provides methods for treating an individual having an infection or tumor comprising injecting the individual near or at the site of the infection or tumor with an effective amount of professional antigen presenting cells (APCs) which have been genetically modified to enhance the expression of an immunostimulatory cytokine.

In preferred embodiments, the genetically modified APCs are professional antigen presenting cells, and most preferably the PAPCs are dendritic cells selected from the group consisting of CD34+-derived dendritic cells, bone marrow-derived dendritic cells, monocyte-derived dendritic cells, splenocyte derived dendritic cells, skin-derived dendritic cells, follicular dendritic cells, and germinal center dendritic cells. In particularly preferred embodiments, the dendritic cells are CD34+-derived dendritic cells cultured in the presence of at least one factor selected from the group consisting of G-CSF, GM-CSF, TNF-α, IL-4, the Flt-3 ligand and the kit ligand.

In addition, in preferred embodiments, the immunostimulatory cytokine is selected from the group consisting of the interleukins (e.g., IL-1α, IL-1β, IL-2, IL-3, IL-4, IL-6, IL-8, IL-9, IL-10, IL-12, IL-18, IL-19, IL-20), the interferons (e.g., IFN-α, IFN-β, IFN-γ), tumor necrosis factor (TNF), transforming growth factor-β (TGF-β), granulocyte colony stimulating factor (G-CSF), macrophage colony stimulating factor (M-CSF), granulocyte-macrophage colony stimulating factor (GM-CSF), the Flt-3 ligand and the kit ligand.

Further, in preferred embodiments, the APCs have been genetically modified by transduction with a viral vector encoding the immunostimulatory said cytokine and, most preferably, with a retroviral vector. In other embodiments, however, the APCs may be genetically modified with adenoviral vectors or adeno-associated viral vectors, or by lipofection, ballistic injection, or other means of genetic modification known in the art.

Further, in any of the foregoing embodiments, the individual which is treated may suffer from a cancer selected from the group consisting of melanomas, hepatomas, adenocarcinomas, basal cell cancers, oral cancers, nasopharyngeal cancers, laryngeal cancers, bladder cancers, head and neck cancers, renal cell cancers, pancreatic cancers, pulmonary cancers, cervical cancers, ovarian cancers, esophageal cancers, gastric cancers, prostate cancers, testicular cancers, breast cancers, or other solid tumors. Alternatively, the individual may suffer from a refractory infection.

BRIEF DESCRIPTION OF THE DRAWINGS

FIGS. 1(A+B) shows the time course of IL-12 production by IL-12-gene modified BM-DCs. (A) After transduction on day 4, supernatant in DC culture with GM-CSF and IL-4 was collected daily and assayed in an IL-12 ELISA. (B) Day 6 BM-DCs transduced with IL-12 gene were harvested, washed twice, and recultured at $10^6$ cells/ml to evaluate IL-12 production. Open circles indicate non-transduced cells, open triangles indicate DFG-hCD80-neo transduced cells, and solid circles indicate DFG-mIL-12 transduced cells.

FIGS. 2(A–C) shows the changes in area of established (A) MCA205, (B) B16, and (C) D122 tumors after injection of HBSS (open circles), $10_6$ Zeo-transduced (triangles) and IL-12-transduced (solid circles) BM-DCs into the tumors. Data are presented as mean±SE.

FIGS. 6(A+B) shows (A) the tumor-specific CTL activity of splenocytes from mice treated with HBSS (open circles), Zeo- (triangles) and IL-12- (squares) transduced BM-DCs and IL-12-transduced fibroblasts (solid circles) against MCA205, and (B) CTL activity by splenocytes from mice injected with IL-12-transduced BM-DCs against MCA205 (open circles), YAC-1 (triangles) and syngeneic fibroblasts (squares).

FIGS. 7(A+B) shows the effect of intratumoral injection of HBSS (open circles), Zeo-transduced (triangles) and IL-12-transduced (solid circles) BM-DCs on the area of (A) injected and (B) non-injected, contralateral MCA205 or B16 tumors. Data are presented as mean±SE.

DETAILED DESCRIPTION OF THE INVENTION

Definitions

In order to more clearly and concisely point out and describe the subject matter which applicants consider as the invention, the following definitions are provided for certain terms used in the written description and appended claims.

As used herein, the term "antigen-presenting cell" or the abbreviation "APC" means a cell that can process a protein antigen, break it into peptides, and present it in conjunction with MHC molecules on the cell surface, where it may interact with appropriate T cell receptors. The term antigen presenting cell, as used herein, is intended to encompass both professional and non-professional antigen presenting cells.

As used herein, the term "professional antigen-presenting cell" or the abbreviation "PAPC" means an antigen presenting cell with highly efficient immunostimulatory capacity. PAPCs display antigenic peptide fragments in association with the proper class of MHC molecules and also bear costimulatory surface molecules. Different classes of PAPCs include Langherhans' cells, interdigitating cells (IDCs), follicular dendritic cells (FDCs), germinal center dendritic cells (GCDCs), B cells, and macrophages.

As used herein with respect to the APCs of the invention, a "genetically modified" APC means an APC into which, or into an ancestor or precursor of which, has been introduced an exogenous nucleic acid which is transcribed and translated to produce molecules encoded by the introduced nucleic acid, or which integrates into the genome of an APC and enhances the transcription and/or translation of endogenous nucleic acid sequences encoding an immunostimulatory cytokine. The term "genetically modified" may be used herein to embrace any method of introducing exogenous nucleic acids including, but not limited to, transformation, transduction, transfection, and the like.

As used herein, a coding sequence and a regulatory region are said to be "operably joined" when they are covalently linked in such a way as to place the expression or transcription of the coding sequence under the influence or control of the regulatory region. If it is desired that the coding sequences be translated into a functional protein, two DNA sequences are said to be operably joined if induction of promoter function results in the transcription of the coding sequence and if the nature of the linkage between the two DNA sequences does not (1) result in the introduction of a frame-shift mutation, (2) interfere with the ability of the regulatory region to direct the transcription of the coding sequences, or (3) interfere with the ability of the corresponding RNA transcript to be translated into a protein. Thus, a regulatory region would be operably joined to a coding sequence if the regulatory region were capable of effecting transcription of that DNA sequence such that the resulting transcript might be translated into the desired protein or polypeptide.

As used herein with respect to the genetically modified APCs of the invention, the term "enhance expression" of an immunostimulatory cytokine means to increase the levels of transcription and/or translation of nucleic acid sequences encoding the cytokine.

As used herein, the term "immunostimulatory cytokine" means a soluble molecule which mediates interactions amongst immune system cells and, in particular, causes an activation or increase in an immune response against an antigenic peptide presented by an APC. Particularly intended are immunostimulatory cytokines selected from the group consisting of the interleukins (e.g., IL-1α, IL-1β, IL-2, IL-3, IL-4, IL-6, IL-7, IL-8, IL-9, IL-10, IL-12, IL-18, IL-19, IL-20), the interferons (e.g., IFN-α, IFN-β, IFN-γ), tumor necrosis factor (e.g., TNF-α), transforming growth factor-β (TGF-β), granulocyte colony stimulating factors (G-CSF), macrophage colony stimulating factor (M-CSF), granulocyte-macrophage colony stimulating factor (GM-CSF), the Flt-3 ligand and the kit ligand. As used herein, references to any of these cytokines are intended to embrace the human homologs and any other mammalian homologs having activity in humans substantially similar to the human protein.

I. Methods of Treatment

The present invention derives, in part, from the discovery that antigen-presenting cells (APCs), which have been genetically modified to enhance expression an immunostimulatory cytokine, may be directly injected into or near the site of an infection or tumor to induce a specific immunological response against antigens associated with the infection or tumor without pre-loading or pulsing the APCs with the antigens. In particular, it has been found that professional antigen presenting cells, such as dendritic cells (DCs), and more preferably bone marrow-derived dendritic cells (BM-DCs) or CD34+-derived dendritic cells (CD34+-DCs), which have been genetically modified to enhance expression an immunostimulatory cytokine, preferably interleukin-12 (IL-12), may be injected into or near the site of an infection or tumor to induce a specific immune response against antigens associated with the site of injection. Significantly, in experiments involving injection into tumors, it has been found that professional antigen presenting cells, such as DCs engineered to constitutively express IL-12 can cause tumor regression, both at the site of injection and at distant sites, and can induce tumor-associated antigen (TAA) specific Th1 cell responses in both regional lymph nodes and the spleen.

Thus, in general, the present invention provides methods of treatment for subjects, particularly human subjects, having an infection or tumor, in which APCs, preferably professional antigen presenting cells, genetically modified to enhance expression an immunostimulatory cytokine are injected into or near the site of the infection or tumor. Thus, the methods comprise the steps obtaining a sample of APCs, genetically modifying the APCs to enhance expression an immunostimulatory cytokine, and injecting the genetically modified APCs, preferably professional antigen presenting cells, into or near the site of an infection or tumor. Before or after genetically modifying the APCs, and before injecting them, they may be clonally expanded by standard techniques of cell culture which are well known in the art. If the APCs are to be autologous, the steps of obtaining and modifying the cells, as well as optionally clonally expanding the cells, is preferably performed as close as possible to the time of injection. If, however, heterologous but syngeneic APCs are to be used, the cells may be obtained and genetically modified far in advance of injection, and may be maintained indefinitely prior to use.

Subjects for treatment with the methods of the present invention include cancer patients and subjects with refractory infections. Because it is preferred that the genetically-modified APCs, preferably professional antigen presenting cells, are injected directly into the site of a tumor or infection, it is expected that the present methods will be most useful in subjects having at least one physically well-defined tumors or a physically well-defined site of an infection, rather than a diffuse, highly metastasized cancer or diffuse infection. On the other hand, as shown in the examples below, injection into one site at which a tumor (or infection) is present, can lead to the development of a systemic immune response. Therefore, the methods of the present invention may be effective in treating diffuse, highly metastasized cancers or diffuse infections if at least one site of a tumor or infection can be identified at which the APCs, preferably professional antigen presenting cells, can be injected and can effectively load tumor-associated or infection-associated antigens.

In currently preferred embodiments, the methods of the present invention are used to treat patients having solid tumors, into which the genetically modified APCs, preferably professional antigen presenting cells, of the invention may be directly injected. Appropriate solid tumors may include melanomas, hepatomas, adenocarcinomas, basal cell cancers, oral cancers, nasopharyngeal cancers, laryngeal cancers, bladder cancers, head and neck cancers, renal cell cancers, pancreatic cancers, pulmonary cancers, cervical cancers, ovarian cancers, esophageal cancers, gastric cancers, prostate cancers, testicular cancers, and breast cancers. For many of these cancers, an association between DC infiltration and prognosis has been established.

The genetically modified APCs of the invention may be injected using standard sterile techniques for subcutaneous, intradermal, transdermal, intramuscular, intraperitoneal or other forms of injection. The cells may be administered in a physiologically acceptable solution or buffer and may be administered in combination with other agents, particularly cytokines, which may promote the ability of the APCs to survive, load antigen, traffic to the draining lymph nodes or spleen, and present antigen to activate an immune response. The number of cells to be introduced depends upon a number of factors, including the number of sites to be injected, the number of injections which are to be performed over time, the size of the tumor or infectious lesion, and the nature of the tumor or infection. Although the number of cells to be used will vary with such factors, it is presently expected that $10^4$–$10^8$, preferably $10^5$–$10^7$, cells will be injected per site per treatment.

Details and currently preferred embodiments relating to the choice and isolation of APCs, choice of immunostimulatory cytokines, and genetic modification of the APCs, are described separately below.

II. Choice and Isolation of APCs

The present invention employs antigen presenting cells APCs, preferably professional antigen presenting cells, most preferably, dendritic cells, which have been genetically modified to enhance expression of an immunostimulatory cytokine.

Preferably, the original source of the APCs is the subject to be treated, such that the APCs are autologous. Allogeneic APCs, obtained from other individuals, may also be employed in the present invention, but preferably the APCs are derived from histocompatible or syngeneic individuals so as to provide proper MHC presentation to the cognate, antigen-specific T cell receptors of the subject. In addition, genetically engineered animals, such as mice or pigs, may be created which express human or humanized MHC proteins, and optionally co-stimulatory molecules, and may be used as a renewable source of APCs capable of proper MHC presentation to the cognate, antigen-specific T cell receptors of the subject.

Preferred PAPCs are dendritic cells, and particularly CD34+-derived DCs (CD34+DCs) harvested from mobilized peripheral blood, and bone marrow-derived dendritic cells (BM-DCs) harvested from bone marrow. Other DCs which may be useful in the invention include monocyte-derived DCs harvested from blood, CD34+-DCs harvested from bone marrow, splenocyte derived DCs harvested from the spleen, skin-derived DCs, follicular dendritic cells (FDCs), and germinal center dendritic cells (GCDCs). Methods of isolating these dendritic cells from the tissues in which they arise and or localize are well known in the art. For example, methods for isolating BM-DCs are described in Inaba et al. (1992), *J. Exp. Med.* 176:1693–1702. Alternatively, CD34+ progenitor cells may be obtained from human umbilical cord or adult blood, and may be stimulated with cytokines to differentiate into dendritic cells (see, for example, Caux et al. (1996) *J. Exp. Med.* 184:695–706; Romani et al. (1994), *J. Exp. Med.* 180:83–93). The effectiveness of the Flt-3 ligand in generating dendritic cells is described in, for example, Shurin et al. (1997), *Cell Immunol.* 179:174–184. BM-DCs or CD34+-DCs cultured with GM-CSF and IL-4 for several (e.g., 5 days) are particularly preferred. TNF-α and the kit ligand have also been shown to be effective in to increase the yield of DCs grown in culture (see, e.g., Mayordomo et al. (1997), *Stem Cells* 15:94–103, and references cited therein), and may be used to obtain the DCs of the present invention. A majority of such DCs may display the immature phenotype as determined by flow cytometry and MLR assay in accordance with previous reports (Pierre et al. (1997), *Nature* 388:787–792; Inaba et al. (1993), *J. Exp. Med.* 178:479–488). DCs have antigen-capturing and processing as well as trafficking abilities only during their immature phase (Pierre et al. (1997), *Nature* 388:787–792; Inaba et al. (1993), *J. Exp. Med.* 178:479–488; Cella et al. (1997), *Nature* 388:782–787).

III. Choice of Cytokines

The APCs of the present invention are genetically modified to enhance expression of an immunostimulatory cytokine. Preferably, the cytokine is one of the interleukins (e.g., IL-1α, IL-1β, IL-2, IL-3, IL-4, IL-6, IL-7, IL-8, IL-9, IL-10, IL-12, IL-18, IL-19, IL-20), the interferons (e.g., IFN-α, IFN-β, IFN-γ), tumor necrosis factor (TNF), transforming growth factor-β (TGF-β), granulocyte colony stimulating factors (G-CSF), macrophage colony stimulating factor (M-CSF), granulocyte-macrophage colony stimulating factor (GM-CSF), the Flt-3 ligand or the kit ligand. The amino acid sequences of these cytokines are well known in the art. Thus, an amino acid sequence of interleukin-4 may be found in, for example, Arai et al. (1989), *J. Immunol.* 142(1):274–282; an amino acid sequence of interleukin-6 may be found in, for example, Yasukawa et al. (1987), *EMBO J.* 6(10):2939–2945; amino acid sequences of the p35 and p40 subunits of interleukin-12 may be found in, for example, Wolf et al. (1991), *J. Immunol.* 146(9):3074–3081; amino acid sequences of various IFN-α subtypes may be found in, for example, Gren et al. (1984), *J. Interferon Res.* 4(4):609–617, and Weismann et al. (1982), *Princess Takamatsu Symp.* 12:1–22; an amino acid sequence of TNF may be found in, for example, Pennica et al. (1984), *Nature* 312:724–729; an amino acid sequence of G-CSF may be found in, for example, Hirano et al. (1986), *Nature* 324:73–76; and an amino acid sequence of GM-CSF may be found in, for example, Cantrell et al. (1985), *Proc. Natl. Acad. Sci. (USA)* 82(18):6250–6254. In order to genetically modify APCs to enhance expression of one of these cytokines, one of ordinary skill in the art may choose to use a vector comprising a naturally occurring nucleic acid sequence which encodes the cytokine (e.g., a genomic or cDNA sequence) or may, utilizing the degeneracy of the genetic code, design and produce a vector comprising a non-naturally occurring sequence which still encodes a functional cytokine. In the case of heterodimeric immunostimulatory cytokines (e.g., IL-12), the APCs of the invention must be genetically modified to express both subunits of the cytokine molecule.

The APCs of the invention may also be genetically modified to express variants of these cytokines. For example, for those cytokines having both pro-forms and mature forms (e.g., before and after cleavage of a signal peptide, or before and after limited proteolysis to yield an active fragment), the APCs of the invention may be genetically modified to express either the pro- or mature form. Other variants, such as fusion proteins between an active fragment of a cytokine and a heterologous sequence (e.g., a heterologous signal peptide), may also be employed. Species variants may also be employed to the extent that they retain activity in a human subject. Thus, for example, human APCs may be genetically modified to express a murine, bovine, equine, ovine, feline, canine, non-human primate or other mammalian variant of a human cytokine if these species variants retain activity substantially similar to their human homologues.

IV. Genetic Modification of APCs

The APCs of the invention may be genetically modified by any standard technique known in the art to introduce nucleic acids encoding the desired cytokines. For example, methods of genetic modification of human dendritic cells by retroviral transduction are described in Reeves et al. (1996), *Cancer Res.* 56:5672–5677, and Specht et al. (1997), *J. Exp. Med.* 186:1213–1221. Similarly, genetic modification of bone marrow cells by retroviral-mediated transfer of the IL-4 gene is described in Chambers et al. (1992), *J. Immunol.* 149(9):2899–2905. In addition, retroviral transduction of human CD34$^+$ progenitor cells, with subsequent cytokine stimulation to promote differentiation and maturation into dendritic cells, with or without centrifugation, has been described in Henderson et al. (1996), *Cancer Res.* 56:3763–3770, and Reeves et al. (1996), *Cancer Res.* 56:5672–5677. Use of a retroviral supernatant, instead of co-cultivation with retroviral producer cells (Specht et al. (1997)), has several advantages over other strategies including: (1) there is no direct toxicity to the cells; (2) stable gene expression is attained; (3) there is minimal virus-specific CTL response unlike methods with adenoviral vectors (see, e.g., Smith et al. (1996), *J. Virol.* 70:6733–6740); and (4) there is more extensive clinical experience with the use of retroviral supernatants.

The genetic modification of the APCs of the present invention may be transient or stable. That is, the cytokine-encoding nucleic acid sequences which are introduced into the APCs may exist apart from the cells' genomic DNA and be expressed only temporarily, or they may integrate into the cells' genomes and continue to be expressed throughout the life of the cells. For example, transient expression of IL-6 using adenovirus vectors is described in Richards et al. (1995), *Ann. NY Acad. Sci.* 762:282–292. For transiently expressed sequences, it is preferred that the expression of the immunostimulatory cytokines continue for at least one and preferably several days, to allow adequate time for the APCs to pick up antigen at the site of an infection or tumor, to migrate to regional lymph nodes, and to activate cognate T cells by presentation of antigen.

Preferably the genetic construct which is used to enhance the expression of an immunostimulatory cytokine includes a constitutive promoter which is operably joined to the sequences encoding the cytokine to allow constitutive expression of the cytokine by the genetically modified APCs. Alternatively, however, inducible promoters may be used if the conditions for induction can be met under physiological conditions with or without additional treatment of the subject (e.g., administering an inducer).

In addition to the retroviral methods of genetically modifying APCs described above and in the Examples below, many other methods of producing appropriate vectors, genetically modifying cells with those vectors, and identifying transformants are well known in the art and are only briefly reviewed here (see, for example, Sambrook et al. (1989) *Molecular Cloning: A Laboratory Manual*, 2nd ed., Cold Spring Harbor Laboratory Press, Cold Spring Harbor, N.Y.). A wide variety of vectors have been developed and are commercially available which allow inducible (e.g., Lac-Switch expression vectors, Stratagene, La Jolla, Calif.) or constitutive (e.g., pcDNA3 vectors, Invitrogen, Chatsworth, Calif.) expression of nucleotide sequences under the regulation of an artificial promoter element. Such promoter elements are often derived from CMV or SV40 viral genes, although other strong promoter elements, which are active in eukaryotic cells, can also be employed to induce transcription. Typically, these vectors also contain an artificial polyadenylation sequence and 3' UTR which can also be derived from exogenous viral gene sequences or from other eukaryotic genes. Furthermore, in some constructs, artificial, non-coding, introns and exons may be included in the vector to enhance expression of the cytokine sequence of interest. These expression systems are commonly available from commercial sources and are typified by vectors such as pcDNA3 and pZeoSV (Invitrogen, San Diego, Calif.). Innumerable commercially-available as well as custom-designed expression vectors are available from commercial sources to allow expression of any desired transcript in more or less any desired cell type, either constitutively or after exposure to an exogenous stimulus (e.g., withdrawal of tetracycline or exposure to IPTG).

Vectors may be introduced into the APCs by various methods well known in the art including, but not limited to, calcium phosphate transfection, strontium phosphate transfection, DEAE dextran transfection, electroporation, lipofection (e.g., Dosper Liposomal transfection reagent, Boehringer Mannheim, Germany), microinjection, ballistic injection on micro-beads using a "gene gun", or, for viral vectors, by infection with the recombinant virus.

EXAMPLES

Retroviral Vectors

The construction of retroviruses DFG-mIL-12, TFG-mIL-12 and DFG-hCD80-neo have been described in previous studies (Tahara et al. (1995); Zitvogel et al. (1996), *Eur. J. Immunol.* 26:1335–1341). MFG-EGFP and MFG-Zeo were created by subcloning the respective fragments obtained from pEGFP-N1 (Clontech, Palo Alto, Calif.) and pcDNA3.1/Zeo(−) (Invitrogen, Carlsbad, Calif.) (Cormack et al. (1996), *Gene* 173:33–38). Retroviral supernatant was generated by transfecting these proviral constructs into BOSC23 or BING packaging cell lines (Tahara et al. (1995)). CRE and CRIP cells producing DFG-hCD80-neo retroviruses were created by the infection of these packaging cells with BING or BOSC23-produced retroviruses, respectively with subsequent selection with G418 (Geneticin; Life Technologies, Inc., Grand Island, N.Y.). The titer of retroviral supernatants was calculated from the G418-surviving colonies after the transduction into NIH3T3 cells.

Tumor Cell Lines and Mouse Strains

A variety of transplantable murine tumor cell lines were injected into mice to initiate tumors, which were then treated with the genetically modified APCs of the invention. MCA205 methylcholanthrene-induced fibrosarcoma was generously provided by S. A. Rosenberg (National Cancer Institute, Bethesda, Md.). The B16-F10 murine melanoma cell line was kindly provided by E. Gorelik (University of Pittsburgh, Pittsburgh, Pa.). The D122 highly metastatic variant of 3LL tumor cells was kindly provided by L. Aisenbach (Weizmann Institute of Science, Rehovot, Israel). YAC-1 was a generous gift by W. Chambers (University of Pittsburgh, Pittsburgh, Pa.). These cell lines were maintained in RPMI 1640 supplemented with 10% heat-inactivated fetal bovine serum, 2 mM glutamine, 100 $\mu$g/ml streptomycin, 100 IU/ml penicillin, and $5\times10^{-5}$ M2-ME (all from Life Technologies, Inc., Grand Island, N.Y.), referred to henceforth as complete medium (CM).

Female 6–8-week-old C57BL/6 (B6) mice were purchased from Taconic Farms (Germantown, N.Y.) and used for all experiments at the age of 8 to 10 weeks old.

Culture and Genetic Modification of APCs

BM-DC culture was obtained using methods previously described (Mayordomo et al. (1995); Zitvogel et al. (1996); Inaba et al. (1992), *J. Exp. Med.* 176:1693–1702). Briefly, murine bone marrow cells were harvested from the femur and tibia of sacrificed mice. Contaminating erythrocytes were lysed with 0.83M $NH_4Cl$ buffer and lymphocytes were depleted with the cocktail of antibodies (RA3-3A1/6.1, anti-B220; 2.43, anti-Lyt 2; GK1.5, anti-L3T4; all from American Type Culture Collection, Rockville, Md.) and rabbit complement (Accurate Chemical and Scientific Corp., Westbury, N.Y.) on day 0. These cells were cultured overnight in CM to remove the adherent macrophages, and then non-adherent cells were placed in fresh CM containing rmGM-CSF (1000 U/ml) and rmIL-4 (1000 U/mi) (DC media) on day 1. Cells were generally harvested on day 6. BM-DCs were defined by morphology, phenotype and strong mixed lymphocyte reaction-stimulating activity. Phenotypic analysis by flow cytometry showed high expression of CD11b, CD11c, CD80, CD86, as well as MHC class I and class II in the majority of the cultured cells (60–95%).

For the retroviral transduction, $1\times10^6$ BM cells cultured in DC media for 24 h were aliquoted to 14-ml round bottom tubes and suspended in 1 ml of the retroviral supernatant with 8 $\mu$g/ml polybrene, 1000 U/ml rmGM-CSF and 1000 U/ml rmIL-4. These cells were centrifuged at 2500×g at 30–32° C. for 2 h (Kotani et al. (1994), *Hum. Gene Ther.* 5:19–28; Bahnson et al. (1995), *J. Virol. Methods* 54:131–143). After centrifugation, cells were cultured in DC media. The transduction process was repeated on day 3 and 4. Retroviral supernatant from the ecotropic producer cells, BOSC23 and CRE, transduced murine BM-DCs more effectively when compared with amphotropic viruses at comparable titers. The retroviral supernatants from BOSC23 cells was used because they produced the highest titer of virus ($2-8\times10^6$ cfu/ml). To examine the transduction efficiency of murine BM-DCs, we generated retroviral vectors with inserted human CD80 (B7.1) or EGFP genes as transduction markers and determined the efficiency of transduction by flow cytometry. Retrovirally modified DCs at high transduction efficiency (22–75%) could express the transgenes for at least 12 days after the last transduction (on day 4) in culture. Transduction efficiency was well correlated with the titer of retroviral supernatants used. Two color immunofluorescence staining showed that significant numbers of marker (hCD80)-positive cells also expressed high levels of mCD80 as well as CD86, MHC class II and DEC-205.

Figure 1A:
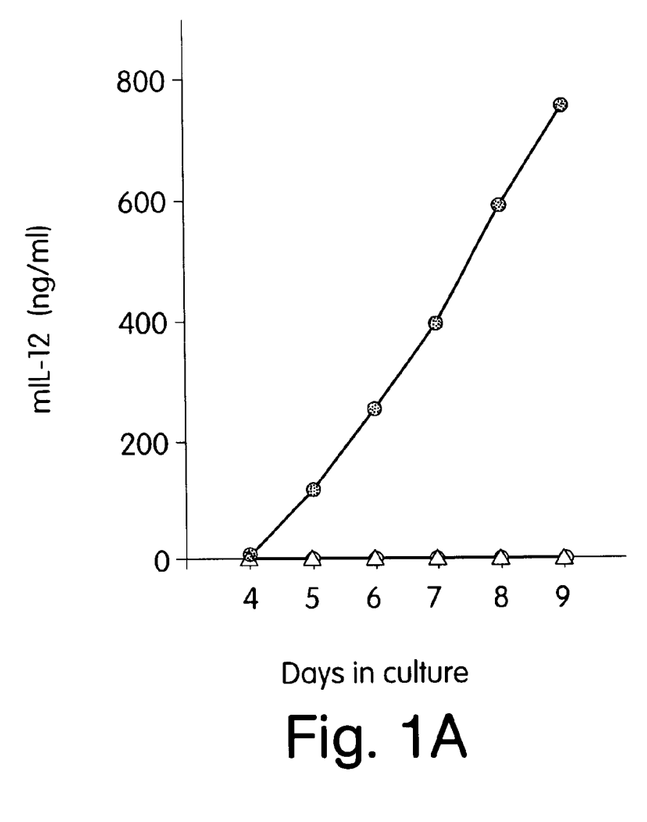
Figure 1B:
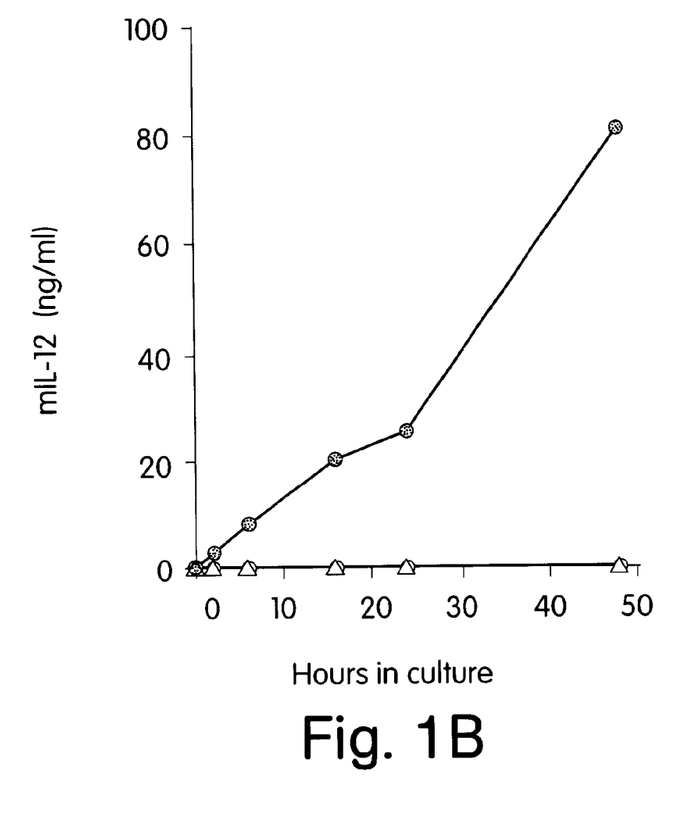

Transduction with the EGFP retroviral vector revealed that murine BM-DCs can be retrovirally transduced at high efficiency. Furthermore, BM-DCs were also transduced with a retroviral vector modified to express both IL-12 genes (DFG-mIL-12). After completion of the transduction procedures on day 4, the concentration of mIL-12 p70 heterodimer in culture media was measured by ELISA. As shown in FIG. 1A, the accumulation of heterodimeric IL-12 (p70) was observed in cultures of DFG-mIL-12-transduced BM-DC, but not in cultures of nontransduced or marker gene-transduced cells. On day 6, DCs were harvested, washed twice and transferred to a new plate. At that time, IL-12-transduced DCs produced approximately 80 ng/$10^6$ cells/48h of heterodimeric IL-12 (FIG. 1B). The range of IL-12 production from IL-12-transduced DCs was 8–80 ng/$10^6$ cells/48h, and was related to the titer of the retroviral supernatant used in each experiment. IL-12 protein produced by the genetically modified DCs was confirmed to be biologically active and capable of stimulating IFN-γ production from Con A-treated splenocytes. To examine the effect of IL-12 transduction on DC phenotype, various cell surface molecules were examined using flow cytometry. IL-12-transduced DCs did not differ from non- or Zeo-transduced DCs except that they expressed increased levels of MHC class I and II molecules.

Culture and Genetic Modification of Fibroblasts

For comparison with the therapeutic effectiveness of the genetically modified APCs of the invention, similarly modified fibroblasts were prepared. In brief, primary culture of syngeneic fibroblasts were obtained from the lungs of B6 mice. Small pieces of lung were minced with scissors, and stirred in a triple enzyme solution of collagenase IV, hyaluronidase V and deoxyribonuclease IV (Sigma, St Louis, Mo.) for 3 h at room temperature. After rinsing twice with HBSS, the cell suspension was cultured in CM to obtain the primary culture of fibroblasts. IL-12-transduced fibroblasts were generated by infection with the supernatant of CRIP-TFG-mIL-12-neo followed by selection with G418.

Intratumoral Injection of Genetically Modified APCs

To produce animal models of cancer patients, mice (four or five animals per group) were injected intradermally in the right flank with $1 \times 10^5$ cells of the MCA205, B16 and D122 tumor lines on day 0. On day 7, when tumor sizes became 10–20 $mm^2$, $10^6$ non-transduced or transduced BM-DCs were injected intratumorally. IL-12-transduced syngeneic fibroblasts were used for intratumoral injection after irradiation (5000 rad) as described previously (Zitvogel et al. (1995)). When mice rejected the established tumor, they were rechallenged with a larger number of tumor cells ($2 \times 10^5$) on the opposite flank to evaluate the induction of protective systemic immunity against tumor;

Suppression and/or Rejection of Established Tumors

Figure 2A:
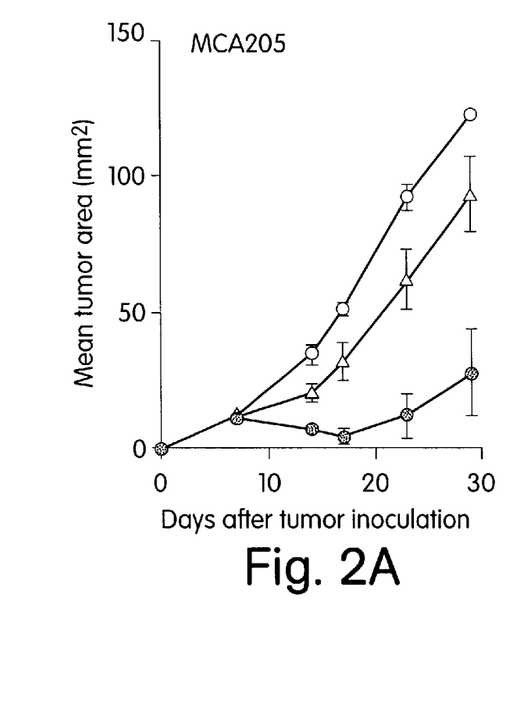
Figure 2B:
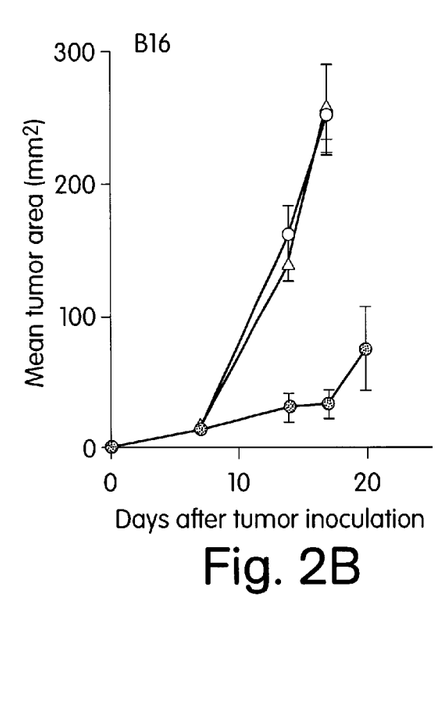
Figure 2C:
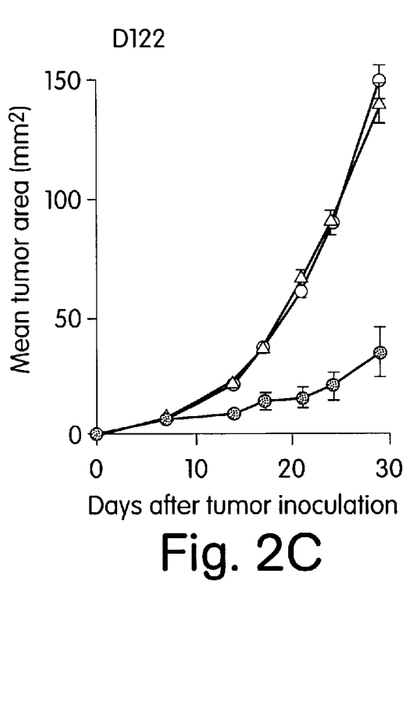
Figure 3:
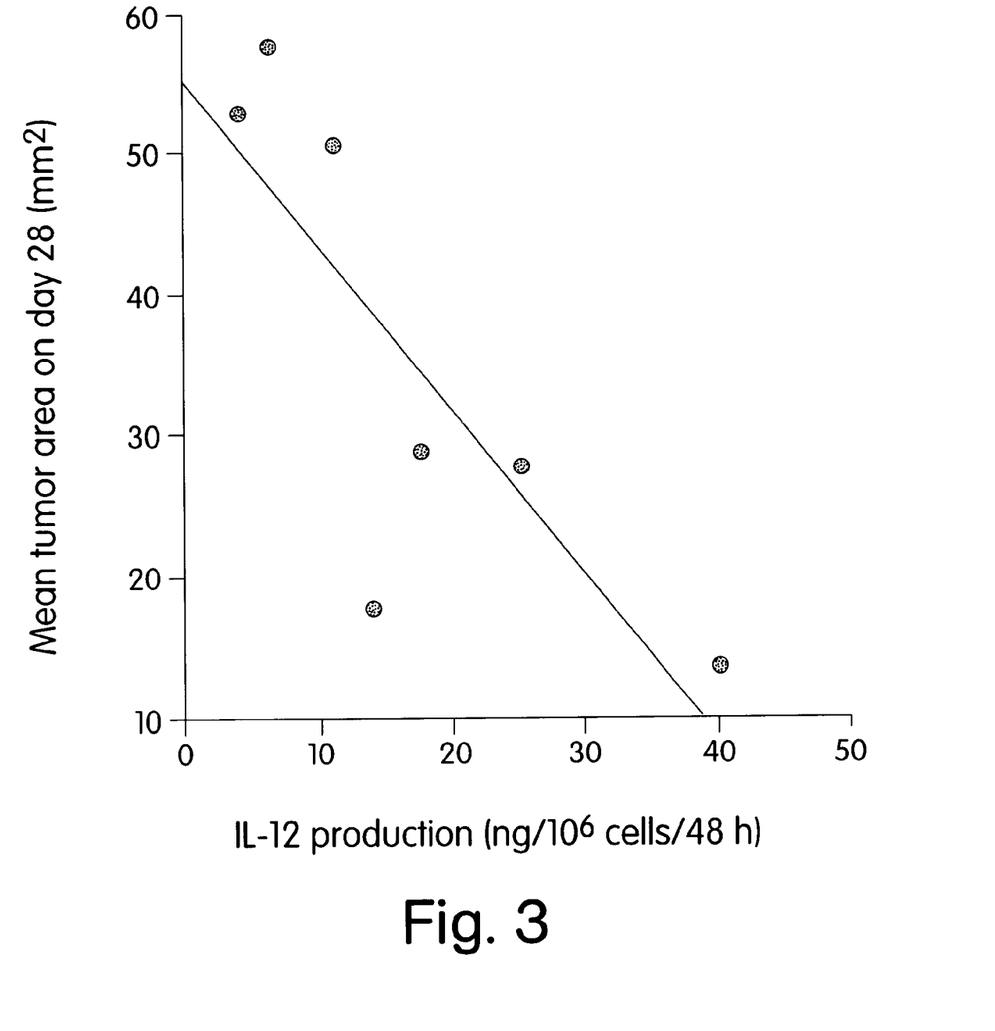
FIG. 3 shows the correlation between IL-12 production by genetically modified DCs and the effect of intratumoral injection of these DCs on the area of MCA205 tumors.
Figure 4:
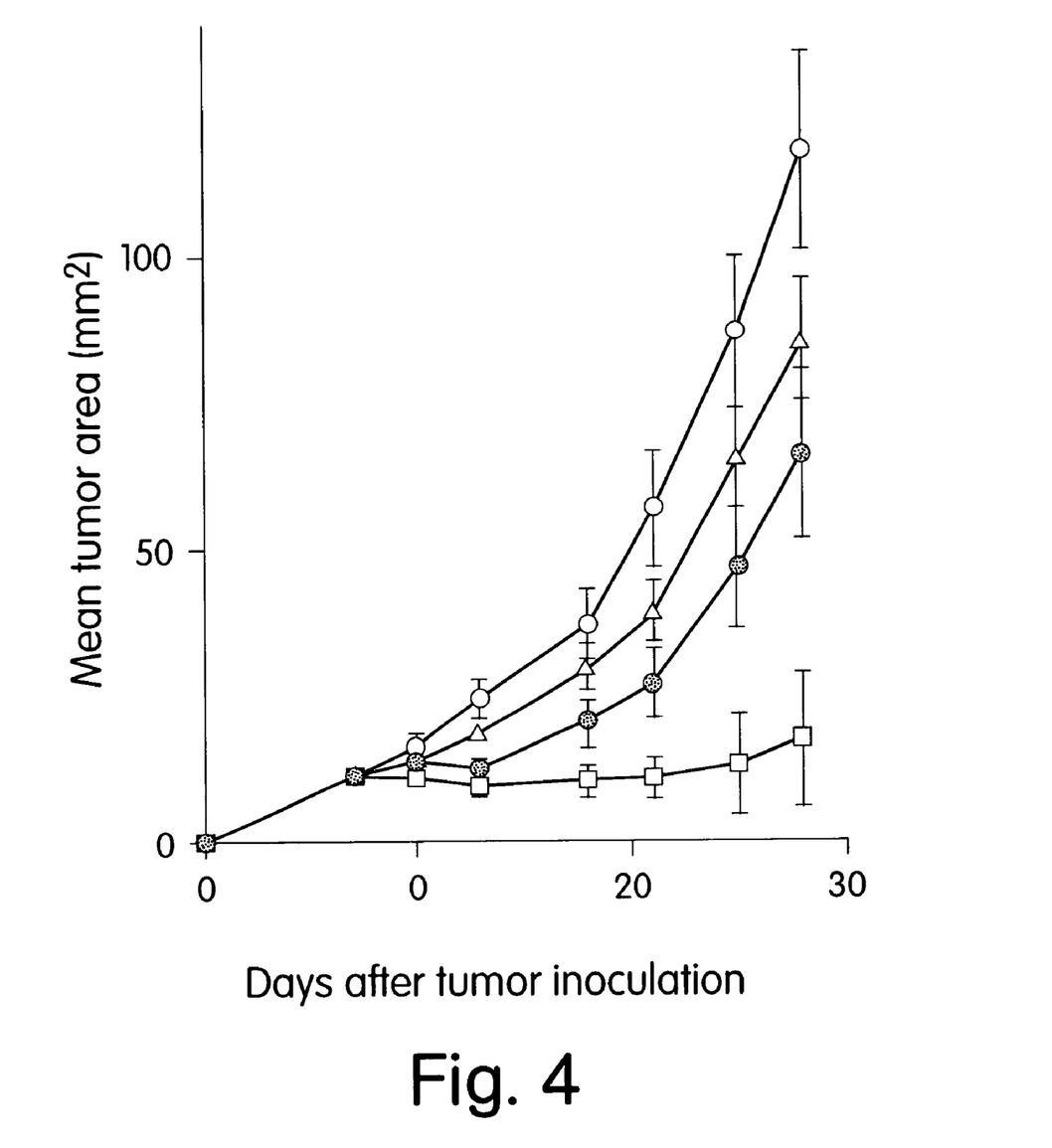
FIG. 4 shows the effect on the growth of established MCA205 tumors of injection of HBSS (open circles), $10^6$ Zeo-transduced (triangles), IL-12-transduced BM-DCs (squares) or IL-12-transduced syngeneic fibroblasts (solid circles). Data are presented as mean±SE.
Figure 5:
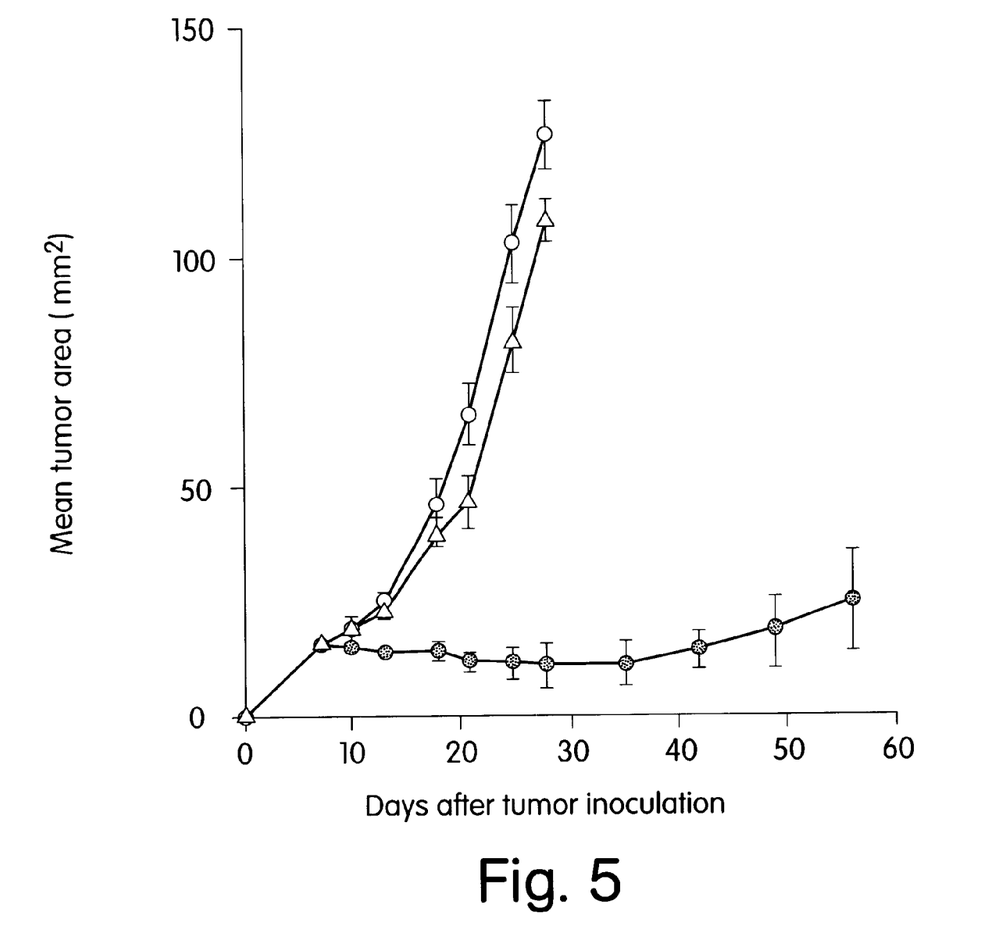
FIG. 5 shows the effect on the growth of established MCA205 tumors of repeated injections of HBSS (open circles), $10^6$IL-12-transduced BM-DCs (solid circles) or IL-12-transduced syngeneic fibroblasts (triangles). Data are presented as mean±SE.

To examine the antitumor effect of intratumoral injection with APCs genetically modified to enhance expression of an immunostimulatory cytokine, $10^6$ nontransduced or IL-12-transduced BM-DCs were injected into the day 7 established tumors (MCA205, B16 and D122) (tumor diameter; 3–5 mm). As shown in FIG. 2, IL-12-transduced DCs significantly suppressed the growth of these established tumors, resulting in eventual rejection in 2 of 5 mice injected with MCA205. Neither non- nor Zeo-transduced DCs had any antitumor effects. In these experiments, IL-12 production of genetically modified DCs was 29 ng/$10^6$ cells/48h. In total, a single treatment with IL-12-transduced DCs resulted in rejection of established MCA205 tumors in 5 of 14 mice (36%). These tumor free mice rejected a subsequent rechallenge with twice as many MCA205, suggesting acquisition of immunological memory for the injected tumor. As shown in FIG. 3, the antitumor effects of IL-12-transduced DCs was correlated ($r=-0.80$, $p<0.05$) with IL-12 production on day 28 using Pearson's linear regression. In another experiment, mice were initially injected i.d. with $1 \times 10^5$ MCA205 cells and then, on day 7, HBSS (open circles), $10^6$ Zeo-transduced (triangles), IL-12-transduced BM-DCs (squares) or IL-12-transduced syngeneic fibroblasts (solid circles) were injected into established tumors. As shown in FIG. 4, the antitumor effect of IL-12-transduced DCs was also compared with that of IL-12-transduced fibroblasts. As previously reported (Zitvogel et al. (1995)), IL-12-transduced fibroblasts suppressed the growth of MCA205, whereas a single injection of them did not show any rejection of tumors. However, IL-12-transduced DCs suppressed tumor growth more efficiently when compared with IL-12-transduced fibroblasts which expressed IL-12 at a similar, but slightly higher level (IL-12 production of genetically modified DCs and fibroblasts was 13 and 22 ng/$10^6$ cells/48h, respectively.). The sequential treatment of intratumoral injection of IL-12-transduced DCs every week was also examined. Briefly, mice were initially injected i.d. with $1 \times 10^5$ MCA205 cells. On days 7 and 14, HBSS (open circles), $10^6$ IL-12-transduced BM-DCs (solid circles), or IL-12-transduced syngeneic fibroblasts (triangles) were injected into established tumors. As shown in FIG. 5, repeated injection of IL-12-transduced DCs resulted in more significant and prolonged regression (over 60 days) of tumor as compared with single injection.

Systemic Tumor-specific Immune Response

As mentioned above, the local antitumor effects of IL-12-transduced DCs were more profound than that observed with IL-12-transduced fibroblasts. To determine whether intratumoral injection of IL-12-transduced DCs could induce significant systemic immune responses specific for the tumor, subcutaneous lymph nodes in the ipsilateral inguinal area of the inoculated tumor (draining lymph nodes) as well as spleen were harvested from tumor bearing mice 7 days after injection with DCs (14 days after tumor inoculation). These lymphoid cells were co-cultured with irradiated tumor cells (MCA205) in vitro, and IFN-γ and IL-4 production in the culture supernatant was examined. Interestingly, injections with non- or Zeo-transduced DCs enhanced tumor specific IFN-γ production by lymphoid cells harvested from draining lymph nodes and spleen when compared with IL-12-transduced fibroblasts. Furthermore, intratumoral injection of IL-12-transduced DCs resulted in greater enhancement of IFN-γ production in response to tumor re-stimulation by these lymphoid cells. Interestingly, DC injection also enhanced IL-4 production to a lesser extent. IFN-γ production was specifically released following MCA205 stimulation, but not with B16 or MCA207 tumors. These results suggest that intratumorally injected DCs transduced with IL-12 traffic to the draining lymph node and efficiently stimulate lymphocytes in situ to produce IFNγ. To confirm this hypothesis, IL-12-transduced DCs were stained with fluorescence dye (PKH-26) and injected intratumorally, and the draining lymph and was examined 24 hours after injection. A significant number of DCs were detected in the draining lymph node 24 h after injection.

Figure 6A:
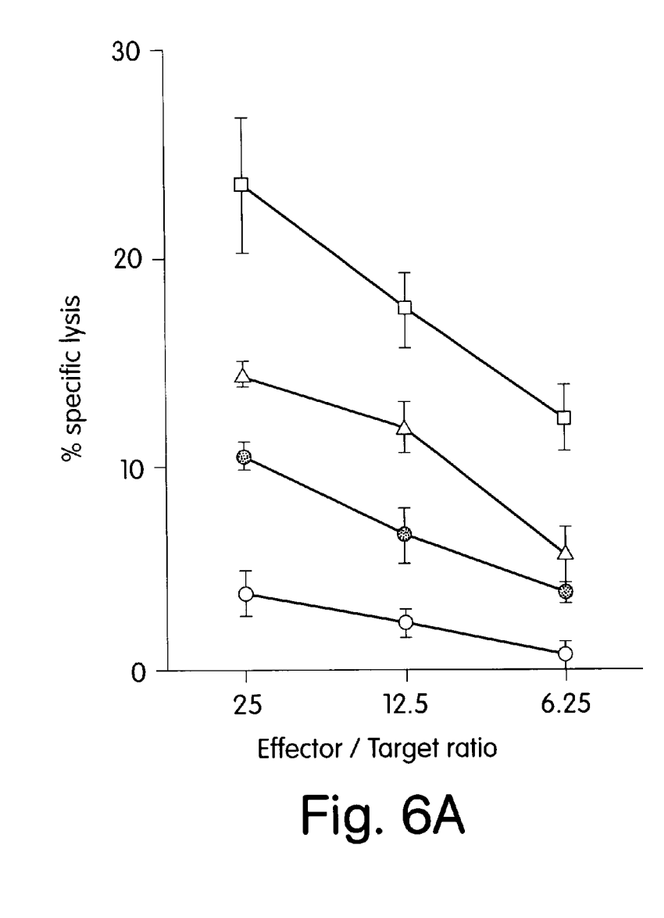
Figure 6B:
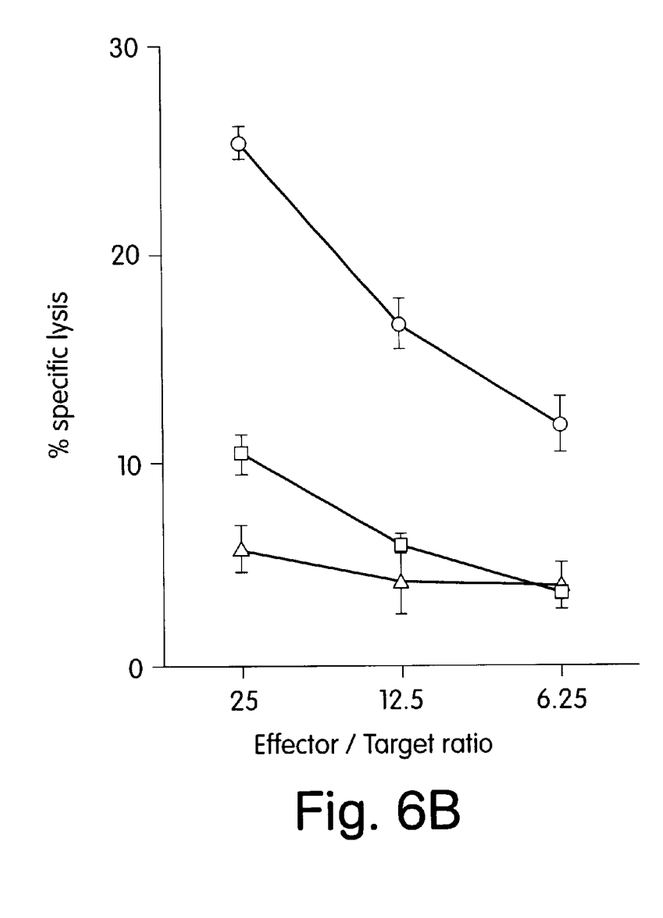

In addition, CTL activity of splenocytes from treated mice was also evaluated. Splenocytes were harvested and pooled from two mice per group 7 days after intratumoral injection with BM-DC. These cells ($2 \times 10^6$) were restimulated in vitro with $2 \times 10^5$ irradiated 5000 rad) MCA205 in the presence of 25 lU/ml of rhIL-2. Restimulated cells were tested 5 days later in a standard $^{51}$Cr-release assay. CTL activities by splenocytes from the groups treated with HBSS, Zeo-transduced and IL-12-transduced BM-DCs, and IL-12-transduced fibroblasts were tested against MCA205 (FIG. 6A). Zeo-transduced DCs were more effective in inducing CTL activity than IL-12-fibroblasts. IL-12-transduced DCs induced significantly higher CTL activity than that observed using any other strategy. CTL activity by splenocytes from mice injected with IL-12-transduced BM-DCs was tested against MCA205, YAC-1 and syngeneic fibroblasts (FIG. 6B). This activity appeared to be specific for the MCA205 tumor and could be blocked 40–50% with anti-CD8 antibody and 24–35% with anti-H-2K$^b$ antibody.

Figure 7A:
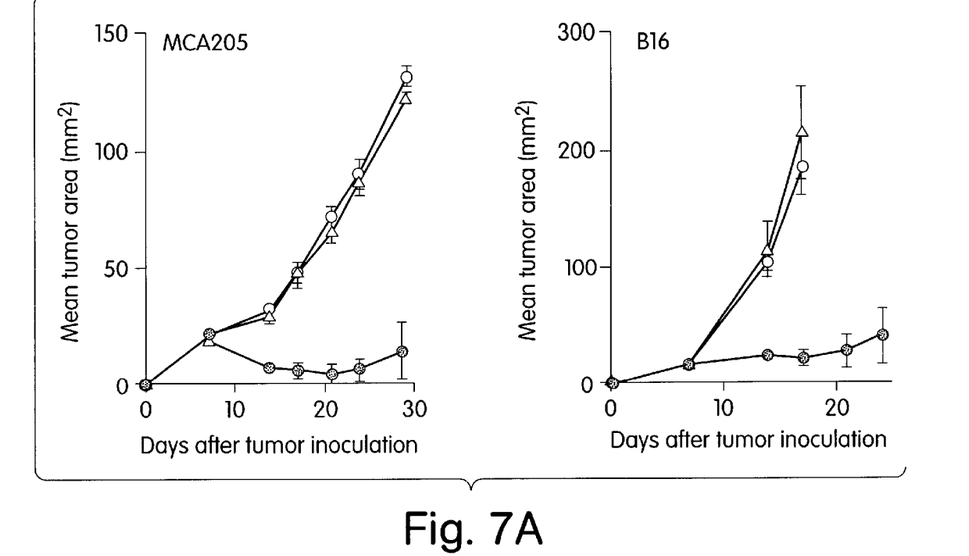
Figure 7B:
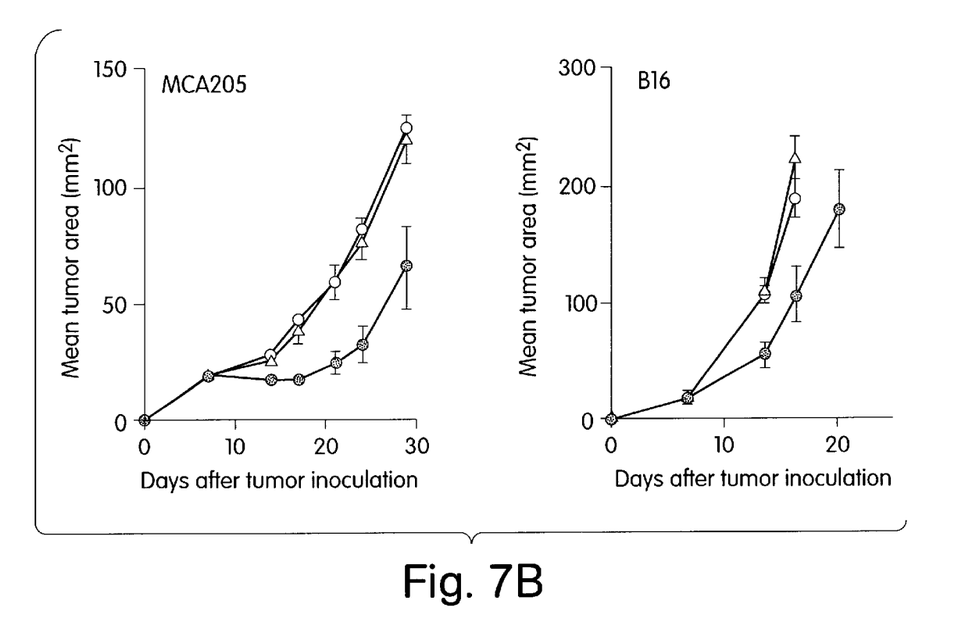

To further confirm the induction of systemic immunity, the growth of a contralateral nontreated tumor was examined. Mice were injected i.d. with 1×10$^5$ MCA205 and B16 tumor cells in both flanks, and IL-12-transduced DCs were injected in the tumor in the right flank on day 7, when tumor area reached 13–20 mm$^2$. Tumor growth in both flanks was monitored. FIG. 7 shows that intratumoral injection with IL-12-transduced DCs significantly suppressed the growth not only of the injected tumor (FIG. 7A) but also of the contralateral, non-injected tumor (FIG. 7B). In these experiments, no IL-12 was detected in murine sera 2 days after injection with IL-12-transduced DCs.

Flow Cytometry

For phenotypic analysis of BM-DCs, PE- or FITC-conjugated monoclonal antibodies against murine cell surface molecules (CD11b, CD11c, CD80, CD86, Gr-1, H-2K$^b$, I-A$^b$ and appropriate isotype controls, all from PharMingen, San Diego, Calif.) were used. DEC-205 was detected by staining with NLDC-145 antibody (Serotec Ltd., Oxford, UK). The transduction marker hCD80 was stained with FITC-conjugated anti-hCD80 antibody (PharMingen, San Diego, Calif.), which does not cross-react with mouse CD80.

In vitro Cytokine Release Assays

Lymphoid cells were obtained from the draining (inguinal) lymph node and spleen harvested from each of two mice which had received intratumoral injection with BM-DCs 7 days earlier. These cells (2×10$^6$) were co-cultured in 24-well plates with 2×10$^5$ irradiated (5000 rad) MCA205 in the presence of 25 IU/mi rhIL-2 (Chiron, Emeryville, Calif.) for 36 h as described previously (Zitvogel et al. (1996)). The supernatants were collected and assessed in an ELISA for mIFN-γ and mIL-4 expression (PharMingen, San Diego, Calif.). The lower limit of sensitivity for each assay was 18 and 36 pg/ml, respectively.

Cytotoxic T Lymphocyte Assays

Splenocytes were harvested and pooled from two mice per group, 7 days after intratumoral injection with BM-DCs. These cells (2×10$^6$) were restimulated in vitro with 2×10$^5$ irradiated (5000 rad) MCA205 in the presence of 25 IU/ml of rhIL-2. Five days later, re-stimulated cells were used as effectors for the standard 4 h -$^{51}$Cr release assay against MCA205, YAC-1 and syngeneic fibroblasts. In brief, 10$^6$ of each target cell were labeled with 100 μCi of Na$_2$$^{51}$CrO$_4$ for 1 h. After washing twice, these effector and target cells were plated at an appropriate E/T ratio in 96-well round bottom plates. The supernatant (100 μl) was collected after 4 h incubation and the radioactivity was counted with a γ-counter. The percentage of specific lysis was calculated as the following formula: % specific lysis =100 ×(experimental release−spontaneous release)/(maximal release−spontaneous release).

Statistical Analysis

Statistical analysis was performed using the unpaired two-tailed Student's t-test. Pearson's linear regression was applied to examine the correlation. Differences were considered significant when the p value was less than 0.05.

What is claimed is:

1. A method of treating an individual having an tumor comprising:

injecting an individual at or near a site of a tumor with an effective amount of genetically modified dendritic cells which have not been pre-loaded with tumor associated antigen prior to said injection, wherein said dendritic cells have been genetically modified to enhance expression of IL-12 by transduction with a vector encoding IL-12, whereby the injection of said dendritic cells results in the treatment of said tumor.

2. A method as in claim 1 wherein said dendritic cells have been genetically modified by transduction with a viral vector encoding IL-12.

3. A method as in claim 2 wherein said viral vector is a retroviral vector.

4. A method as in claim 2 wherein said viral vector is selected from the group consisting of adenoviral vectors and adeno-associated viral vectors.

5. A method as in claim 3 wherein said dendritic cells have been genetically modified by centrifuging said dendritic cells with the supernatant of producer cells expressing said retroviral vector encoding IL-12.

6. A method as in claim 1 wherein said dendritic cells are selected from the group consisting of CD34+-derived dendritic cells, bone marrow-derived dendritic cells, monocyte-derived dendritic cells, splenocyte derived dendritic cells, skin-derived dendritic cells, follicular dendritic cells, and germinal center dendritic cells.

7. A method as in claim 1 wherein said dendritic cells are CD34+-derived dendritic cells cultured in the presence of at least one factor selected from the group consisting of G-CSF, GM-CSF, TNF-α, IL-4, the Flt-3 ligand and the kit ligand.

8. A method as in claim 1, wherein said dendritic cells are transduced ex vivo.

9. A method as in claim 1, wherein the expression of IL-12 by said dendritic cells results in the reduction in tumor growth.

10. A method as in claim 1, wherein the expression of IL-12 by said dendritic cells results in the delay of tumor growth.

* * * * *

UNITED STATES PATENT AND TRADEMARK OFFICE
CERTIFICATE OF CORRECTION

PATENT NO.      : 6,482,405 B1
DATED           : November 19, 2002
INVENTOR(S)     : Tahara et al.

It is certified that error appears in the above-identified patent and that said Letters Patent is hereby corrected as shown below:

<u>Title page,</u>
Item [60], Related U.S. Application Data, please delete "60/100,048" and insert -- 60/100,468 --.

Signed and Sealed this

Twelfth Day of August, 2003

JAMES E. ROGAN
*Director of the United States Patent and Trademark Office*